United States Patent [19]

Harder

[11] Patent Number: 4,923,787
[45] Date of Patent: May 8, 1990

[54] PHOTOGRAPHIC ELEMENT CONTAINING SCAVENGER FOR OXIDIZED DEVELOPING AGENT

[75] Inventor: John W. Harder, Rochester, N.Y.

[73] Assignee: Eastman Kodak Company, Rochester, N.Y.

[21] Appl. No.: 351,515

[22] Filed: May 12, 1989

Related U.S. Application Data

[63] Continuation-in-part of Ser. No. 184,526, Apr. 21, 1988, abandoned.

[51] Int. Cl.$^5$ ............................................... G03C 1/34
[52] U.S. Cl. ..................................... 430/489; 430/264; 430/448; 430/490; 430/598
[58] Field of Search ............... 430/448, 489, 490, 264, 430/598

[56] References Cited

U.S. PATENT DOCUMENTS

| | | | |
|---|---|---|---|
| 3,700,453 | 10/1972 | Knechel | 430/505 |
| 4,205,987 | 6/1980 | Erikson et al. | 430/216 |
| 4,224,401 | 9/1980 | Takada et al. | 430/437 |
| 4,269,929 | 5/1981 | Nothnagle | 430/264 |
| 4,650,746 | 3/1987 | Simson et al. | 430/438 |
| 4,684,604 | 8/1987 | Harder | 430/375 |

OTHER PUBLICATIONS

Research Disclosure, Feb. 1979, Item No. 17842.

*Primary Examiner*—Paul R. Michl
*Assistant Examiner*—Janet C. Baxter
*Attorney, Agent, or Firm*—Paul L. Marshall

[57] ABSTRACT

A photographic element is described which comprises a compound capable of scavenging oxidized developing agent to prevent stain and fog formation in developed color images.

17 Claims, No Drawings

PHOTOGRAPHIC ELEMENT CONTAINING SCAVENGER FOR OXIDIZED DEVELOPING AGENT

This is a continuation in part of U.S. patent application Ser. No. 184,526 filed Apr. 21, 1988, now abandoned.

This invention relates to a photographic element, and in particular to a color photographic element containing a scavenger compound for oxidized developing agent.

It is known in the art to add a scavenger to a photographic element in order for the scavenger to interact with oxidized developing agent to prevent it from reacting within the element at an undesired location or at an undesired point in time. The presence of oxidized developing agent at an unwanted location can cause stain or fog and thereby affect the quality of the color images obtained.

Known scavengers for oxidized developing agents include ballasted hydroquinone compounds as described in U.S. Pat. No. 3,700,453 wherein the ballasting groups are secondary alkyl substituents having from 9 to 20 carbon atoms. Also known are ballasted sulfonamidophenols such as described in U.S. Pat. No. 4,205,987 and in Research Disclosure, February 1979, Item No. 17842. (Research Disclosure is published by Kenneth Mason Publications, Ltd., The Old Harbourmaster's, 8 North Street, Emsworth, Hampshire P010 7DD, ENGLAND, and is referred to hereinafter simply as "RD"). However, none of these references suggests use of hydrazide type compounds as scavenging agents for oxidized developer moieties.

U.S. Pat. No. 4,684,604 relates to compounds capable of releasing photographically useful groups (PUG). The compounds comprise a hydrazide moiety which is capable of being oxidized to an azo group. The azo group then causes release of the desired PUG. The hydrazide moiety is attached to a heteroatom of a moiety containing the PUG, the attachment being through a link which comprises an acidic group or an active methylene group positioned adjacent to an acidic group. Compounds of the instant invention do not release photographically useful groups; these compounds are therefore more stable, simpler in structure and easier to prepare. Moreover, this patent does not disclose or suggest the use of hydrazide compounds for scavaging oxidized developer moieties.

U.S. Pat. No. 4,224,401 discloses a process for producing high contrast negative silver images utilizing high sensitivity silver bromide or silver bromoiodide emulsions and hydrazide compounds. The hydrazide compounds function as nucleating agents and can comprise substituted phenyl groups. Moreover, the compounds of the '401 patent, whether ballasted or unballasted, do not function as effective scavenger compounds for oxidized developing agents as shown below by comparative data. This U.S. Patent neither discloses nor suggests the use of such hydrazide compounds as scavengers for oxidized developing agents in color photographic elements.

Accordingly, it is desirable to reduce, or to eliminate, oxidized developing agent remaining in color photographic elements. Prior art hydrazine compounds have not been used or suggested for this purpose.

In accordance with the present invention there is provided a color photographic element which comprises a support, at least one silver halide emulsion layer and a scavenger compound for oxidized developing agent wherein the scavenger compound is a hydrazide having the structural formula:

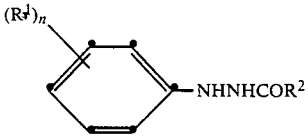

wherein:

$R^1$, represents an electron donating group;

$R^2$ represents hydrogen or alkyl, alkoxy, aryl, aryloxy, aralkyl or amino of the formula $-NHR^3$, where $R^3$ is phenyl or benzyl; with the proviso that at least one of $R^1$ and $R^2$ (a) represents a ballast group of sufficient size as to render the hydrazide compound non diffusible in the photographic element prior to development in alkaline processing solution and (b) comprises a polar group, and n is 1 or 2.

$R^1$ substituents, which are electron donating groups, include alkyl, which can be substituted or unsubstituted, straight or branched chain, having from 1 to about 20 carbon atoms, preferably from about 8 to about 16 carbon atoms; alkoxy, which can be substituted or an unsubstituted, straight or branched chain, having from 1 to about 20 carbon atoms, preferably from about 8 to about 16 carbon atoms; carboxy, carbonamido having the formula $NR^4COR^5$; sulfonamido having the formula $NR^4SO_2R^5$; or amino having the formula $-NR^4R^5$ where $R^4$ is hydrogen or alkyl having from 1 to about 8 carbon atoms and $R^5$ is as defined for $R^4$ or is a benzyl or a phenyl group which may be substituted.

$R^2$ substituents which are alkyl or alkoxy can be as defined for these same substituents in $R^1$, or $R^2$ can be aryl or aryloxy having from 6 to about 10 ring carbon atoms, such as phenyl, phenoxy, naphthyl or naphthoxy.

When $R^2$ represents phenyl or phenoxy it is preferred that the aryl ring have a hydrogen bonding substituent in a position ortho to the point of attachment of the carbonyl group to a hydrazide nitrogen atom. Preferred hydrogen bonding groups include hydroxy, primary or secondary amino groups of the formula $-NR^4R^5$, sulfonamido of the formula $-NHSO_2R^4$, carbonamido of the formula $-NR^4COR^5$ and ureido of the formula $-NHCONHR^4$ where $R^4$ and $R^5$ can be hydrogen or alkyl of from 1 to about 8 carbon atoms and $R^5$ is as defined for $R^4$ or a benzyl or phenyl group.

These groups can also be present as substituents on $R^2$ alkyl groups.

A polar group which can represent $R^1$ or $R^2$ can be a single group or a combination of groups which have a $\pi$ constant which is more negative than $-1.0$. The $\pi$ constant is defined by C. Hansch, A. Leo, S. Unger, K. Hwan Kim, D. Nikaitani and E. T. Lien, in JOURNAL OF ORGANIC CHEMISTRY, 11, 1973 (pp. 1207–1216). The $R^1$ or $R^2$ polar group or groups include, but are not limited to,

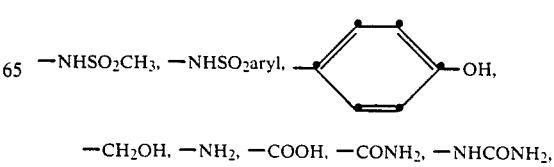

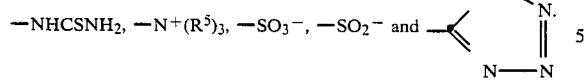, 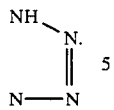

These groups tend to increase the surfactant nature of the hydrazine during alkaline processing.

The alkyl, alkoxy, aryl, aryloxy, aralkyl and benzyl groups which are represented by one or more of $R^1$, $R^2$, $R^3$, $R^4$ and $R^5$ can be substituted with halogen atoms, for example chlorine, or with haloalkyl groups, for example trifluoromethyl, or with

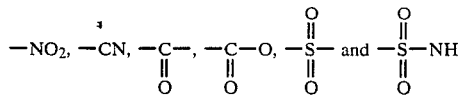

Typical compounds which fall within the above-presented structural formula include:

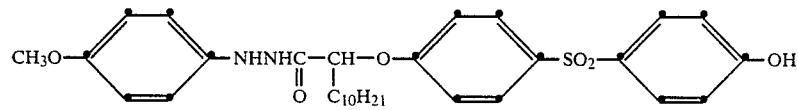

1.

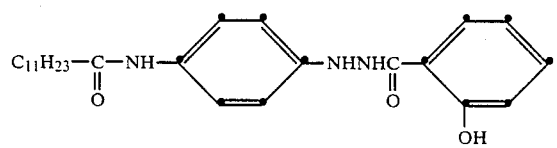

2.

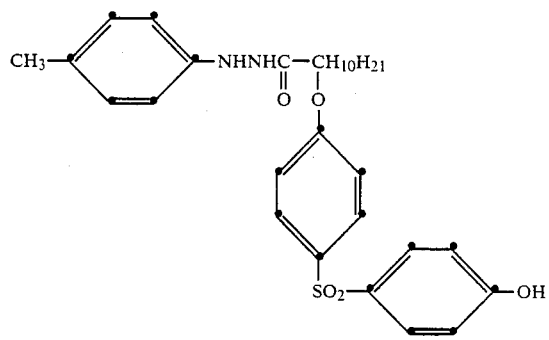

3.

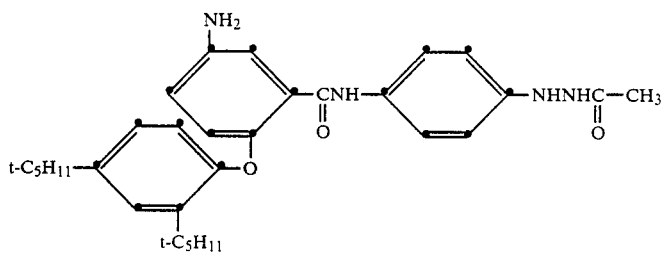

4.

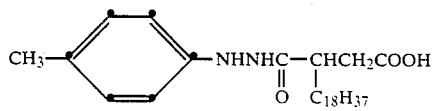

5.

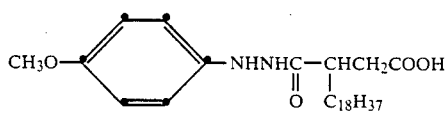

6.

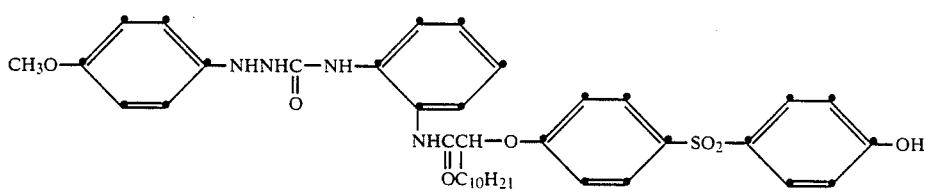

7.

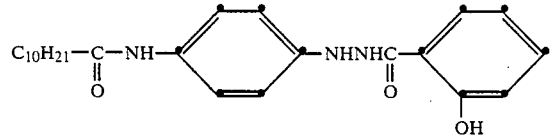
8.
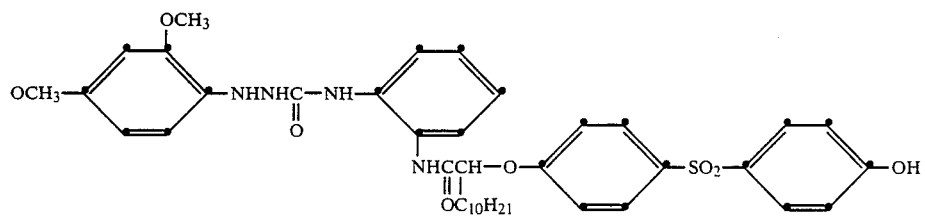
9.
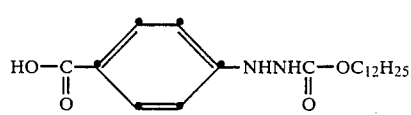
10.
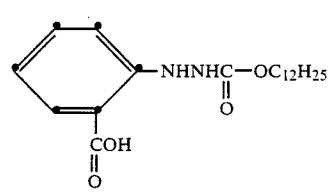
11.
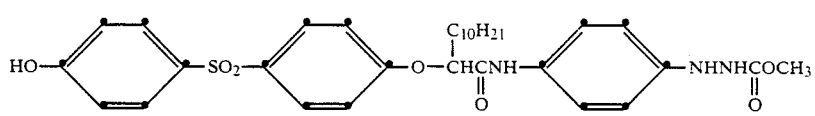
12.
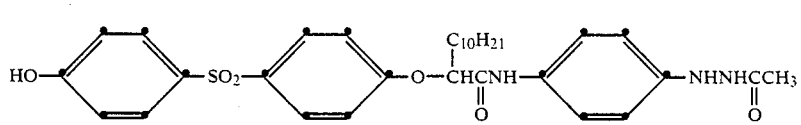
13.
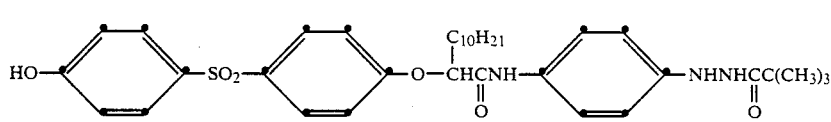
14.
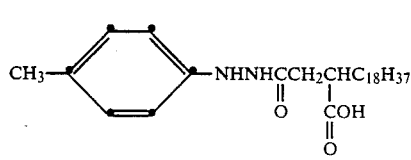
15.
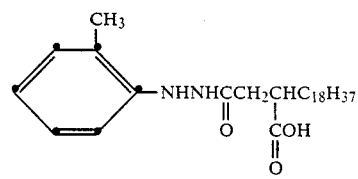
16.
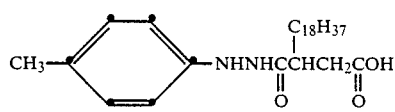
17.
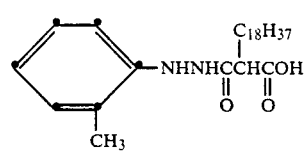
18.

19.
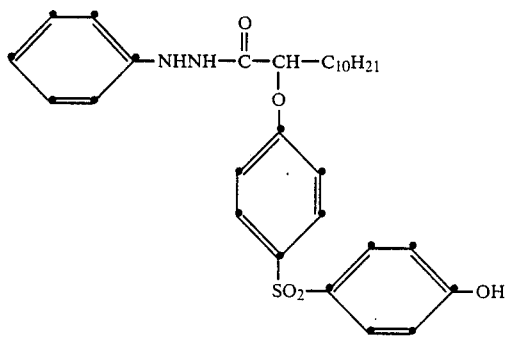
20.
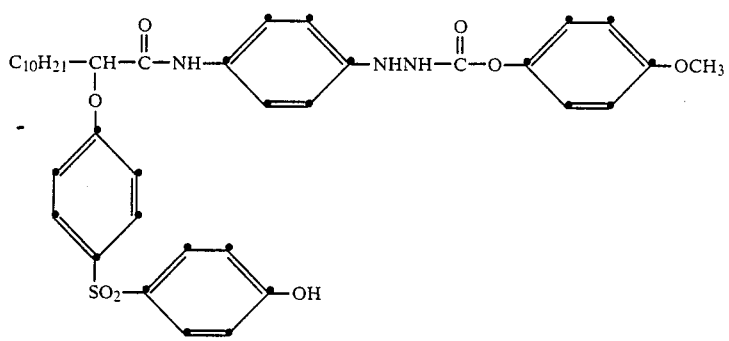
21.
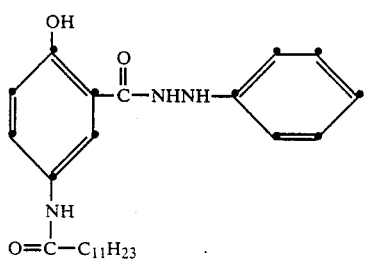
22.
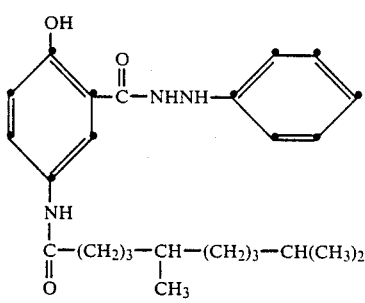

23.
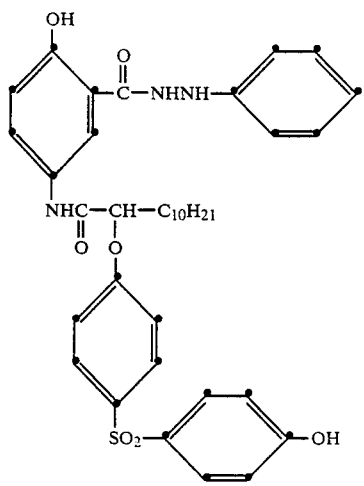
24.
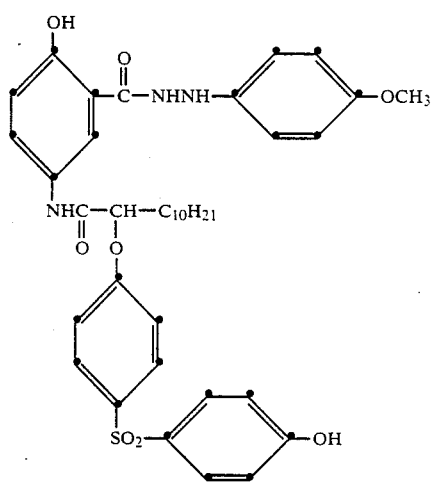
25.
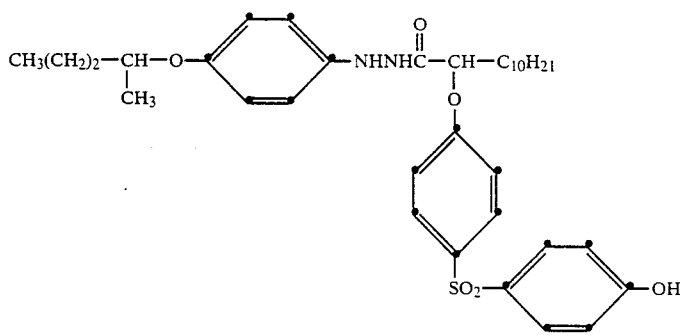
26.
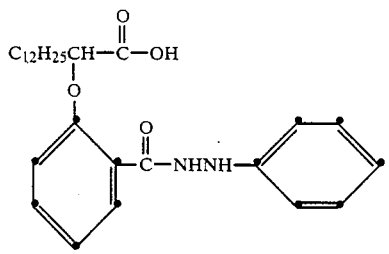
27.
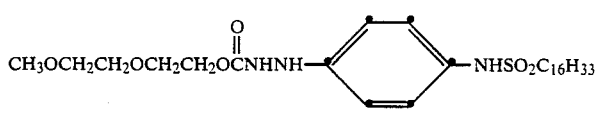

-continued
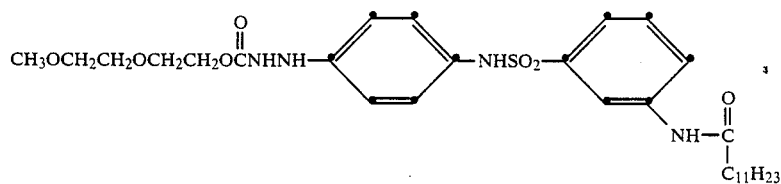
28.
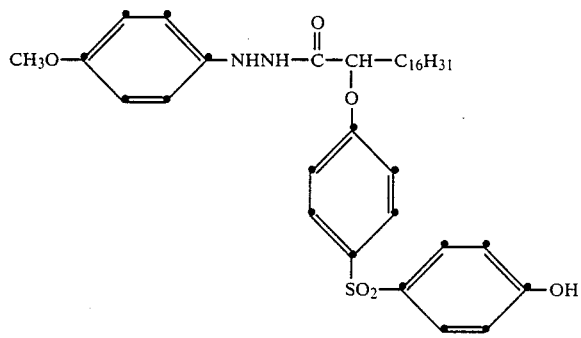
29.
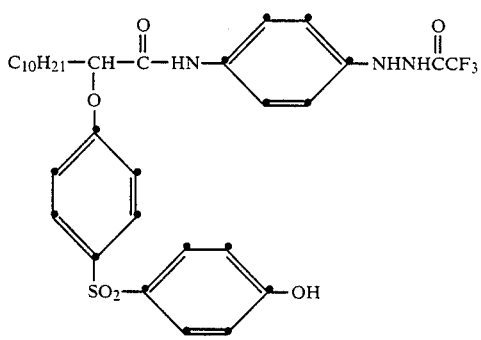
30.
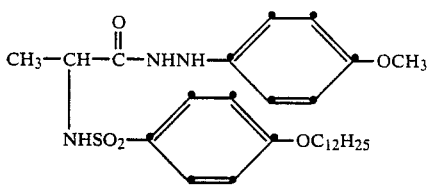
31.
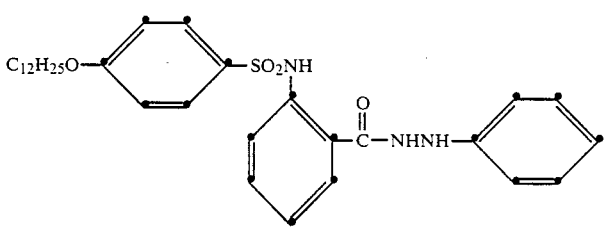
32.
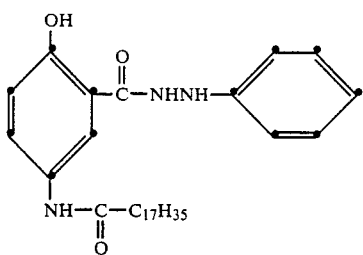
33.

-continued
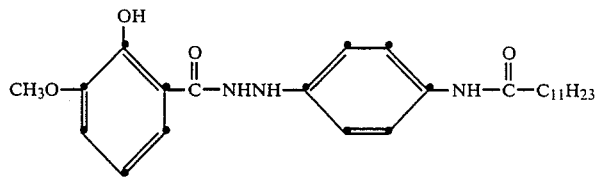
34.
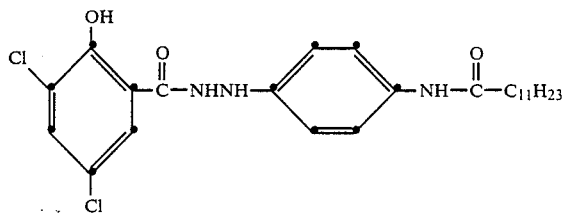
35.
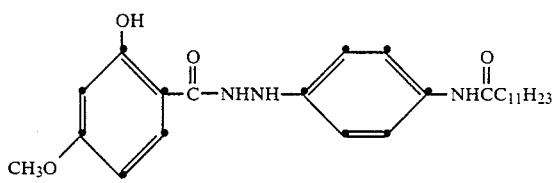
36.
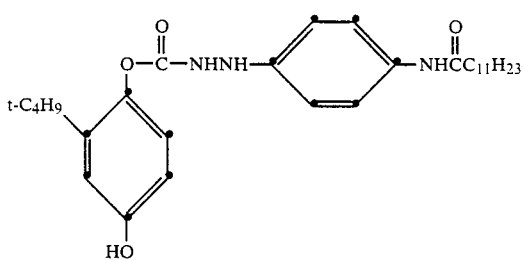
37.
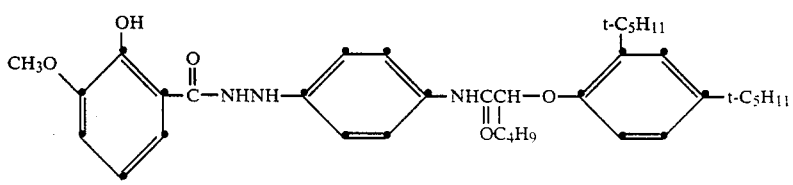
38.
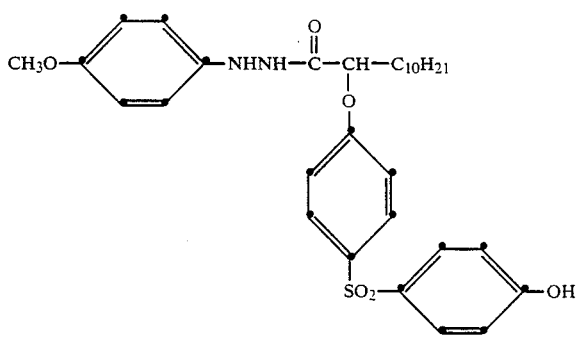
39.

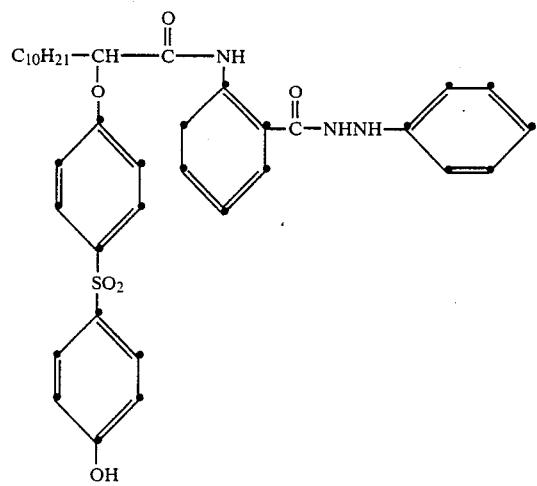
40.
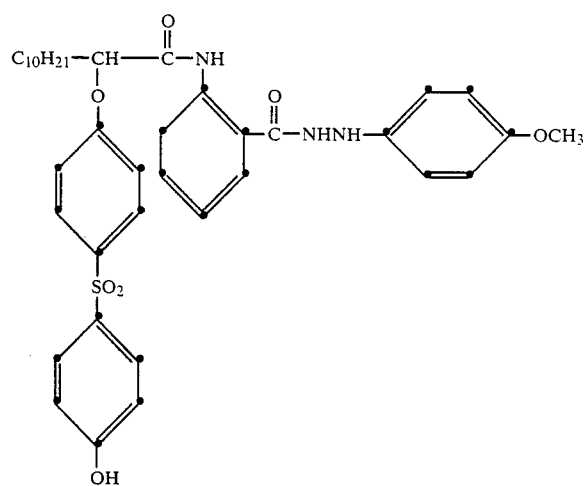
41.
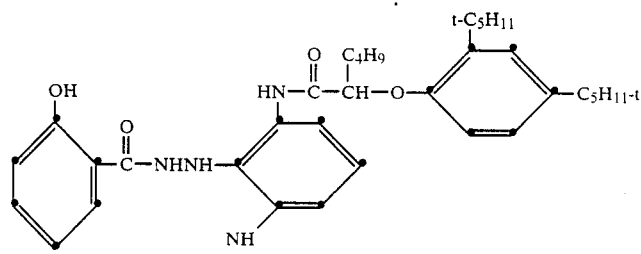
42.
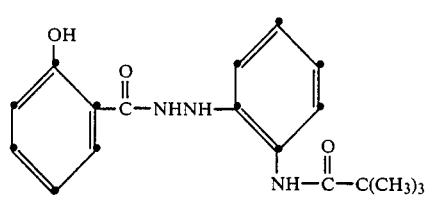
43.

-continued

44.
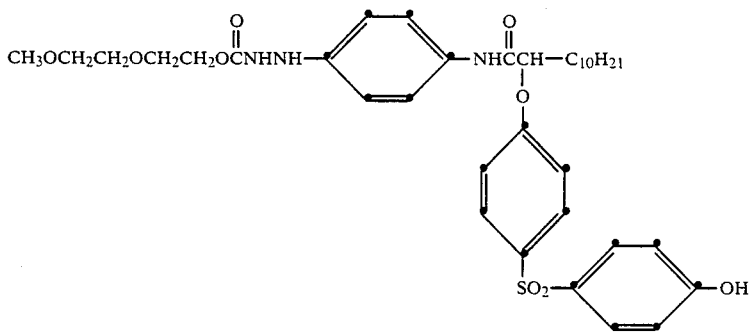

45.
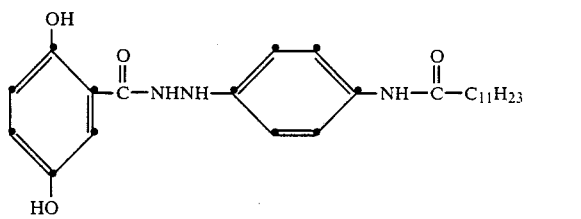

46.
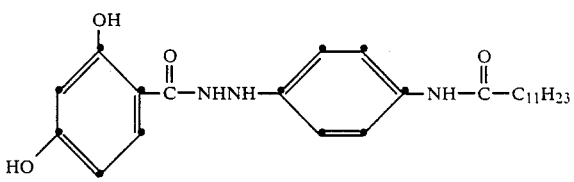

47.
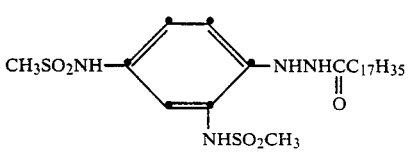

48.
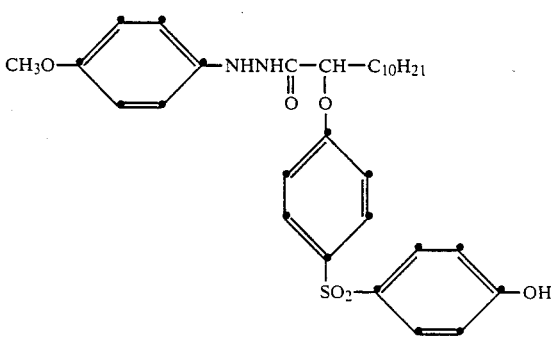

The compounds of the present invention are either known per se or are structurally similar to known compounds. Their preparation can be accomplished using existing technology. For example, Compound No. 1 is prepared according to the following procedure:

SYNTHESIS OF COMPOUND NO. 1

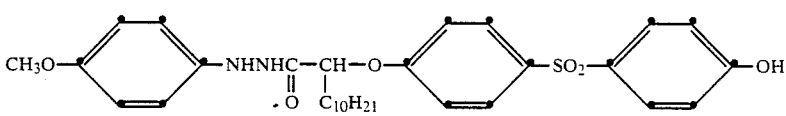

p-methoxyphenylhydrazide hydrochloride (5.0 g) was dissolved in acetonitrile (200 ml) treated with N,N dimethylaniline (10 g) and cooled to <10° C. under nitrogen. The 2-(4-(4-acetoxyphenylsulfonyl)-phenoxy)dodecyl chloride was dissolved in tetrahydrofuran (THF) (50 ml) and added dropwise over a 15 minute period. The reaction mixture was allowed to warm to room temperature while stirring for 2 hours. The reaction was partitioned with ethyl acetate (EtOAc) and 10% HCl. The organic layer was washed again with 10% HCl, dried with MgSO4 and concentrated to a thick oil.

The thick oil was dissolved in 100 ml of methanol and treated with 5 ml of conc HCl and stirred overnight at room temperature. The solution was partitioned between EtOAC and water and the organic layer was washed with water, separated, dried with MgSO₄ and concentrated to a thick oil. This oil was dissolved in dichloromethane and concentrated (twice) and finally dissolved in 20 ml of dichloromethane and allowed to stand overnight to crystallize. The solid was collected by filtration and washed with cold methylene chloride and air dried to yield 15 g (48%) of the desired product (mp 148°–150° C.).

SYNTHESIS OF COMPOUND NO. 21

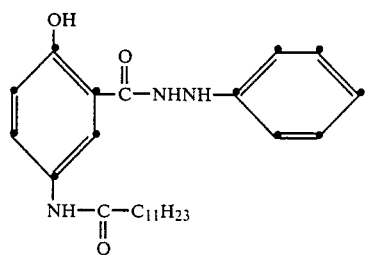

Lauroyl chloride (72.2 g) and pivalic acid (33.7 g) were dissolved in 300 ml of acetonitrile and treated with triethylamine (33.4 g). The reaction mixture was stirred at room temperature for 3 hours. 5-aminosalicyclic acid was added to the reaction mixture and the reaction was stirred at room temperature overnight. The solid which formed was filtered off and washed first with acetonitrile, and then with 10% HCl solution. The resulting product was recrystallized from methanol and dried overnight in the vacuum oven at room temperature.

This compound (10 g) was treated with 50 ml of thionyl chloride and stirred at room temperature for 3 hours and concentrated to a thick oil. The thick oil was dissolved in 50 ml of tetrahydrofuran and added dropwise to a solution of phenylhydrazine (3.2 g) and N,N dimethaniline (3.6 g) in tetrahydrofuran cooled by a dry ice acetone bath. The resulting reaction mixture was kept cold and stirring for three hours. A solution of aqueous 10% HCl (200 ml) was added and the reaction mixture was brought to room temperature. The reaction mixture was partitioned with ethyl acetate. The organic layer was washed with 10% HCl solution (200 ml), dried with magnesium sulfate and concentrated. The product was purified by column chromatography on silica gel to yield 9 g (70%) of the desired product mp (153° C).

SYNTHESIS OF COMPOUND NO. 27

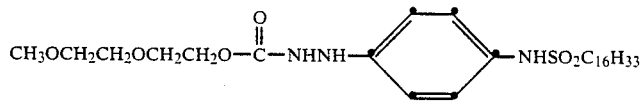

To a round bottom flask containing methoxyethoxyethanol was added phosgene in toluene. This reaction mixture was stirred under nitrogen at room temperature overnight and the reaction was concentrated to one third volume. This solution was added dropwise to a solution of p-nitrophenyl hydrazine hydrochloride (32.2 g) and N,N dimethyl aniline (41.2 g) in acetonitrile (300 ml) and the reaction was stirred at room temperature for 3 hours. The reaction mixture was partitioned with ethyl acetate and 10% HCl solution. The organic layer was washed with 10% HCl solution, dried with magnesium sulfate and then concentrated to a solid. This material (15 g) was taken up in tetrahydrofuran (50 ml) and treated with 2 g of 10% palladium on carbon and shaken with hydrogen at 40 psi overnight. The reaction was treated with hexadecylsulfonylchloride (16.2 g) and triethylamine (5.1 g) and stirred at room temperature for 3 hours.

The reaction mixture was filtered through super cell, and then partitioned with ethyl acetate and 10% HCl. The organic layer was washed with 10% HCl, dried with magnesium sulfate and concentrated down.

The product was purified with column chromatography using a 30% ethyl acetate/70% dichloromethane solvent system to yield 19 g (68%) of the desired product (mp 82° C.).

The scavengers of this invention can be used in the ways and for the purposes that scavengers for oxidized developing agent are employed in the art. For example, they can be incorporated in an interlayer between silver halide emulsion layers sensitive to different regions of the visible spectrum. Alternatively, they can be in a layer comprising a color forming material or in a layer comprising other photographic addenda, such as for example, a layer containing a filter dye or a reflecting agent or a mordant. When incorporated in a separate layer, such layer can also be an undercoat layer positioned between all of the silver halide emulsion layers and a support. The separate layer can also be an overcoat layer positioned above all of the silver halide emulsion layers.

The amount of scavenger compound employed will depend upon the particular purpose for which the scavenger is to be used and the degree of scavenging desired. Typically useful results are obtained when the scavenger is employed in an amount of between about 5 to about 2000 mg/meter₂.

The scavenger can be incorporated in photographic elements by techniques known in the art. In certain embodiments, the scavenger can be dissolved in a high boiling solvent, such as a water insoluble coupler solvent, and then dispersed either in a silver halide emulsion layer or in a separate vehicle such as gelatin. Typical useful coupler solvents are moderately polar solvents such as tritolylphosphate, di-n-butylphthalate, diethyl lauramide and 2,4-dipentylphenol. Typical vehicles are gelatin and other hydrophilic colloids commonly employed in silver halide photographic elements. These vehicles are described in RD, December 1978, Item No. 17643, Section IX. The scavengers can be introduced into the element in a polymeric latex. Suitable techniques for dispersing the scavengers in a latex are described in U.S. Pat. Nos. 4,203,716 and 4,214,047 and in RD, July 1977, Item 15930 and July 1980, Item 19551.

Multicolor photographic elements employed in this invention contain dye image forming units sensitive to each of the three primary regions of the spectrum. Each unit can be comprised of a single emulsion layer or of multiple emulsion layers sensitive to a given region of the spectrum. The layers of the element, including the layers of the image forming units, can be arranged in various order as is known in the art. In an alternative format, the emulsion or emulsion layers can be disposed as one or more segmented layers, e.g., as by the use of microvessels or microcells, as described in U.S. Pat. No. 4,362,806.

A preferred photographic element according to this invention comprises a support bearing at least one blue sensitive silver halide emulsion layer having associated therewith a yellow image dye-providing material, at least one green sensitive silver halide emulsion layer having associated therewith a magenta image dye providing material and at least one red sensitive silver halide emulsion layer having associated therewith a cyan image dye providing material, the element also containing a scavenger of this invention.

The elements of the present invention can contain additional layers conventional in photographic elements, such as overcoat layers, spacer layers, filter layers, antihalation layers, PH lowering layers (sometimes referred to as acid layers), neutralizing layers, timing layers, opaque reflecting layers and opaque light absorbing layers. The support can be of any material known to be suitable for use with photographic elements. Typical supports include polymeric films, paper (including polymer coated paper), metal or glass. Details regarding supports and other layers of the photographic elements useful in this this invention are contained in RD, December 1978, Item 17643, referred to above.

The light sensitive silver halide emulsions employed in the photographic elements of this invention can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide, and mixtures thereof. The emulsions can be, for example, tabular grain light sensitive silver halide emulsions. The emulsions can be negative working or direct positive emulsions. They can form latent images predominantly on the surface of the silver halide grains or in the interior of the silver halide grains. They can be chemically and spectrally sensitized in accordance with usual practices. The emulsions typically will be gelatin emulsions although other hydrophilic colloids can be used in accordance with usual practice. Details regarding the silver halide emulsions are contained in RD, Item 17643, December 1978 and the references listed therein.

The photographic silver halide emulsions can contain other addenda conventional in the photographic art. Useful addenda are described, for example, in RD, December 1978, Item 17643. Useful addenda include spectral sensitizing dyes and desentizers, antifoggants, masking couplers, DIR couplers, DIR compounds, anti stain agents, image dye stabilizers, absorbing materials such as filter dyes and UV absorbers, light scattering materials, coating aids, plasticizers and lubricants, and the like.

Depending upon the dye image providing material employed in the photographic element, such addenda can be incorporated in the silver halide emulsion layer or in a separate layer associated with the emulsion layer. The dye image providing material can be any of a number known in the art, such as dye forming couplers, bleachable dyes, dye developers and redox dye releasers. The particular material employed will depend on the nature of the element and the type of image desired.

Dye image providing materials employed with conventional color materials designed for processing with separate solutions are preferably dye forming couplers; i.e., compounds which couple with oxidized developing agent to form a dye. Preferred couplers which form cyan dye images are phenols and napthols. Preferred couplers which form magenta dye images are pyrazolones and pyrazolotriazoles. Preferred couplers which form yellow dye images are benzoylacetanilides and pivalylacetanilides.

The developing agents which can be used to develop the photographic elements of this invention, the oxidized form of which can be reduced by the scavengers of this invention, include hydroquinones, aminophenols, 3-pyrazolidones and phenylenediamines. Some of these developing agents, when used for certain applications, are referred to in the art as electron transfer agents. The particular developing agent employed will depend on the particular type of photographic element to be processed. For example, phenylenediamines are the developers of choice for use with color photographic elements containing dye forming couplers, while 3-pyrazolidones are frequently used with image transfer materials containing redox dye releasers.

Representative developing agents include: hydroquinone, N-methylaminophenol; 1-phenyl-3-pyrazolidone; 1-phenyl-4,4-dimethyl-3-pyrazolidone; 1-phenyl-4-methyl-4-hydroxymethyl-3-pyrazolidone; N,N-diethyl-p-phenylenediamine;-3-methyl-N,N-diethyl-p-phenylenediamine; 3-methoxy-N,N-diethyl-p-phenylenediamine; and N,N,N',N'-tetramethyl-p-phenylenediamine.

The term "non-diffusible" used herein has the meaning commonly applied to the term in photography and denotes materials that for all practical purposes do not migrate or wander through organic colloid layers of a photographic element, such as gelatin, when the element is processed in an alkaline medium, preferably when processed in a medium having a pH of 10 or greater. The term "diffusible" has the converse meaning and denotes the materials having the property of diffusing effectively through the colloid layers of photographic elements in an alkaline medium.

The term "associated therewith" as used herein is intended to mean that the materials can be in either the same or different layers so long as the materials are accessible to one another during processing.

The following examples further illustrate this invention.

EXAMPLE 1

Compounds of the invention were evaluated in a two layer format (imaging layer and overcoat). The imaging layer was coated on a cellulose acetate support and consisted of 1.5 g/m$^2$ gelatin, 1.1 g/m$^2$ of image Coupler A, 1.75 g per Ag mole of tetraazaindene compound (4-hydroxy-6-methyl-1,3,3a,7 tetraazaindene), 0.75 g/m$^2$ of silver halide emulsion and a compound of this invention in the amount indicated in Table I. Each emulsion was comprised of silver bromoiodide grains (2% iodide; 0.53 micron) which were given sensitized with Dyes B and C noted below. The overcoat consisted of 2.0 g/m$^2$ of gelatin. The coatings were hardened with bis(vinylsulfonylmethyl)ether at a level of 1.75% of the total gelatin. Saponin was used as a surfactant in both layers. The compounds were dispersed at a 1:2 ratio in N,N-diethyldecanamide using cyclohexanone (1:3 ratio) as auxillary solvent. The dispersions were washed for 6 hours prior to coating.

Portions of the coatings were placed in a bomb containing air at 4000 psi (27,580 Pa) and 50° C., and held for 6, 40, and 72 hours. The strips were then extracted to determine the amount of compound still remaining.

Stability results were as follows:

TABLE I

| Invention Compound No. | | Percent Compound Remaining | | |
|---|---|---|---|---|
| | $mg/m^2$ | 6 hours | 40 hours | 72 hours |
| 1 | 240 | 100% | 93% | 87% |
| 2 | 76 | 95% | 84% | 79% |

Coupler A

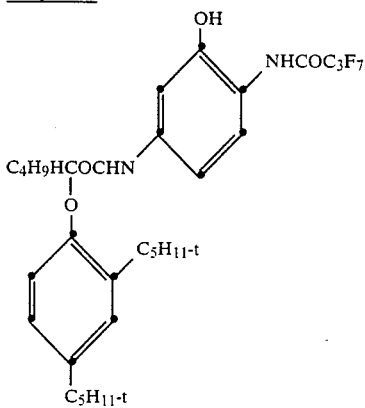

SENSITIZING DYE B

Anhydro-5,5',6,6'-tetrachloro-1,1',3-triethyl-3'-(3-sulfobutyl) benzimidazolocarbocyanine hydroxide

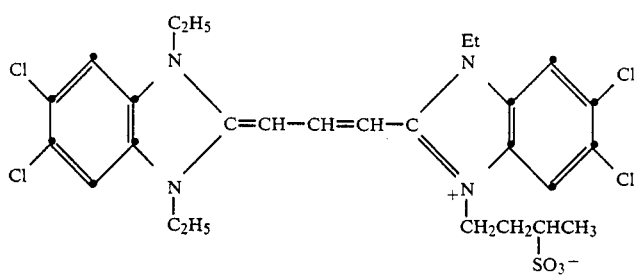

SENSITIZING DYE C

Anhydro 5,5'-dichloro-9-ethyl-3,3'-di(3-sulfopropyl)oxacarbocyanine hydroxide, sodium salt

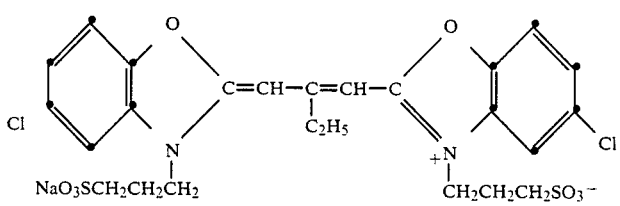

From the above data it can be seen that compounds of this invention are stable under the conditions of the test and that decomposition is avoided. Decomposition results in stain formation in the imaging layers.

EXAMPLE 2

Additional tests were run using coatings prepared as described in Example 1. The purpose of these tests was to show the effects of compounds of this invention on dye density values.

Each example was exposed using a 21 step tablet ranging from 0 to 3.0 density in steps of 0.15 with a 5500K illuminant for 0.02 sec. through a Wratten 8 filter.

The compounds tested were coated at two levels, 0.17 $mmol/m^2$ and 0.2 $mmol/m^2$, which levels correspond to 10 and 25 mol % of the amount of coupler coated. Results from the higher coating level are reported in Table II.

TABLE II

| Compound | Decrease in Density | | | Stain Increase | |
|---|---|---|---|---|---|
| No | (Step 7) | (Toe) | (Step 15) | Blue | Green |
| Control | | | | | |
| (None) | 0 | 0 | 0 | 0 | 0 |
| A (1) | .00 | .02 | .00 | .05 | .00 | .00 |
| B (2) | .03 | .04 | .04 | .30 | .02 | .02 |
| 13 | .08 | .17 | .41 | .61 | .04 | .03 |
| 3 | .08 | .14 | .19 | .42 | .04 | .03 |
| 1 | .19 | .34 | .23 | .64 | .04 | .02 |
| 21 | .17 | .27 | .17 | .40 | .04 | .03 |
| 22 | .18 | .24 | .24 | .46 | .04 | .03 |
| 23 | .14 | .17 | .21 | .33 | .03 | .02 |
| 24 | .14 | .20 | .24 | .41 | .04 | .04 |
| 25 | .15 | .21 | .32 | .66 | .04 | .03 |
| 27 | .12 | .13 | .14 | .43 | .04 | .03 |
| 38 | .20 | .28 | .44 | .80 | .04 | .03 |
| 39 | .16 | .32 | .22 | .48 | .06 | .03 |

(1) Compound A is Compound 4 of column 7 of U.S. Pat. No. 4,224,401
(2) Compound B is Compound 5 of column 7 of U.S. Pat. No. 4,224,401

As can be seen from the above data compounds if this invention, even when coated at 0.42 $mmol/m^2$, cause minimal blue or green stain, whereas the compounds of the prior art either failed to perform or performed at a substandard level.

This invention has been described in detail with particular reference to preferred embodiments thereof, but it will be understood that variations and modifications can be effected within the spirit and scope of the invention.

What is claimed is:

1. A color photographic element comprising a support, at least one silver halide emulsion layer and a scavenger compound for oxidized developing agent wherein the scavenger compound is a hydrazine having the structural formula:

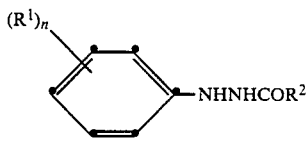

wherein:
$R^1$ represents an electron donating group;
$R^2$ represents hydrogen, alkyl, alkoxy, aryl, aryloxy, aralkyl or amino of the formula —$NHR^3$, where $R^3$ is phenyl or benzyl; with the proviso that at least one of the substituents $R^1$ and $R^2$ (a) represents a ballast group of sufficient size as to render the hydrazide compound non-diffusible in the photographic element prior to development in alkaline processing solution and (b) comprises a polar group having a $\pi$ constant which is more negative than $-1.0$, and n is 0, 1 or 2.

2. The photographic element of claim 1 wherein at least one $R^1$ substituent is an alkyl or alkoxy group having from 1 to about 20 carbon atoms, or a carboxy, carbonamido, sulfonamido or amino group.

3. The photographic element of claim 2 wherein $R^1$ is carbonamido of the formula —$NR^4COR^5$ where $R^4$ is hydrogen or alkyl of from 1 to about 8 carbon atoms and $R^5$ is as defined for $R^4$ or a benzyl or phenyl group.

4. The photographic element of claim 2 wherein $R^1$ is sulfonamido of the formula $NR^4SO\ R^5$ where $R^5$ is hydrogen or alkyl of from 1 to about 8 carbon atoms and $R^5$ is as defined for $R^4$ or a benzyl or phenyl group.

5. The photographic element of claim 2 wherein $R^1$ is amino of the formula —$NR^4R^5$ wherein $R^4$ is hydrogen or alkyl of from 1 to about 8 carbon atoms and $R^5$ is as defined for $R^4$ or is benzyl or phenyl.

6. The photographic element of claim 2 wherein $R^1$ is alkyl or alkoxy having from about 8 to about 16 carbon atoms.

7. The photographic element of claim 1 wherein $R^2$ is alkyl or alkoxy having from 1 to about 20 carbon atoms.

8. The photographic element of claim 7 wherein $R^2$ is alkyl or alkoxy having from about 8 to about 16 carbon atoms.

9. The photographic element of claim 1 wherein $R^2$ is aryl or aryloxy having from 6 to about 10 ring carbon atoms.

10. The photographic element of claim 1 wherein $R^2$ is phenyl or phenoxy.

11. The photographic element of claim 10 wherein the phenyl or phenoxy ring is substituted with a hydrogen bonding group in a position ortho to the point of attachment of the carbonyl group to a hydrazide nitrogen atom.

12. The photographic element of claim 11 wherein the hydrogen bonding group is hydroxy, primary or secondary amino of the formula —$NR^4R^5$, sulfonamido of the formula $NHSO_2R^4$, carbonamido of the formula —$NHCOR^4$ or ureido of the formula —$NHCONHR^4$, where $R^4$ is hydrogen or alkyl of from 1 to about 8 carbon atoms and $R^5$ is as defined for $R^4$ or a benzyl or phenyl group.

13. The photographic element of claim 1 wherein the scavenger compound is present in a layer located between silver halide emulsion layers, in a layer comprising a color forming agent or other photographic addenda, or in an overcoat or undercoat layer.

14. The photographic element of claim 1 wherein the scavenger compound is present in an amount of from about 5 to about 2000 mg/m².

15. The photographic element of claim 1 wherein the scavenger compound has the structural formula:

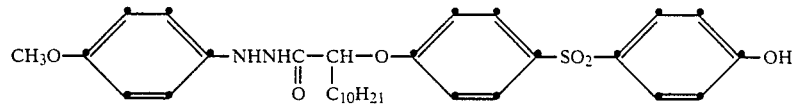

16. The photographic element of claim 1 wherein the scavenger compound has the structural formula:

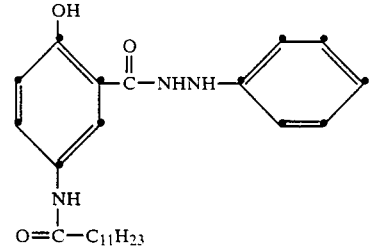

17. The photographic element of claim 1 wherein the scavenger compound has the structural formula:

* * * * *